United States Patent
Choi et al.

[11] Patent Number: 5,919,942
[45] Date of Patent: Jul. 6, 1999

[54] CYCLOHEXANE-1,2,4,5-DIIMIDE DERIVATIVE AND PROCESS FOR PREPARING THE SAME

[75] Inventors: Kil-Yeong Choi; Dong-Hack Suh; Young-Taik Hong; Sang-Hyun Park, all of Daejeon, Rep. of Korea

[73] Assignee: Korea Research Institute of Chemical Technology, Daejeon, Rep. of Korea

[21] Appl. No.: 08/879,977

[22] Filed: Jun. 20, 1997

[30] Foreign Application Priority Data

Jun. 21, 1996 [KR] Rep. of Korea ........................ 96-23500

[51] Int. Cl.⁶ .................................................. C07D 487/04
[52] U.S. Cl. .............................................. 548/429
[58] Field of Search ............................................. 548/429

[56] References Cited

FOREIGN PATENT DOCUMENTS 2417788  10/1975  Germany .

Primary Examiner—Laura L. Stockton
Attorney, Agent, or Firm—Ladas & Parry

[57] ABSTRACT

The disclosure describes a cyclohexane-1,2,4,5-diimide derivative which can be used for the production of colorless transparent polymer and novel engineering plastics having good processability and solubility with an excellent physical property, and a process for preparing the same which comprises reacting a bicyclooctene-1,2,4,5-tetracarboxylic anhydride with alkylamine and aniline derivative and then oxidizing the resulting product with ozone, potassium permanganate, ruthenium chloride hydroxide and aqeous hydrogen peroxide under non-basic condition to convert double bond to dicarboxylic acid or dialdehyde without destroying the imide group.

12 Claims, No Drawings

CYCLOHEXANE-1,2,4,5-DIIMIDE DERIVATIVE AND PROCESS FOR PREPARING THE SAME

FIELD OF THE INVENTION

The present invention relates to a cyclohexane-1,2,4,5-diimide derivative and a process for preparing the same. More specifically, it relates to a novel cyclohexane-1,2,4,5-diimide derivative which can be used as a monomer for high temperature structural and functional polymer, and to a process for preparing the same.

BACKGROUND OF THE INVENTION

Until recently, monomers for preparing transparent engineering plastics and high temperature structural and functional polymers having good solubility and processability have been requested for a long time. In addition, the prior processes for preparing monomers have been less than satisfactory in that the imide group can be destroyed due to the oxidation reaction under basic conditions. The present invention meets such a technical need and ameliorates the problems of the prior art.

SUMMARY OF THE INVENTION

It is an object of the present invention to provide a cyclohexane-1,2,4,5-diimide derivative which has an aliphatic cyclic structure and thus can be used for the preparation of colorless transparent polymer.

It is another object of the invention to provide a process for preparing the cyclohexane-1,2,4,5-diimide derivative.

Other objects and advantages will be apparent to those who have ordinary skill in the art from the following description.

DETAILED DESCRIPTION OF THE INVENTION

The present invention relates to the cyclohexane-1,2,4,5-diimide derivative. The derivative can be used for the production of colorless transparent polymer and novel engineering plastics having good processability and solubility with an excellent physical property because the derivative has an aliphatic cyclic structure and thus do not form a charge-transfer complex after polymerization. Moreover, the introduction of a variety of functional groups to the substituent of cyclohexane-1,2,4,5-diimide can be advantageous in synthesizing functional polymer materials having novel properties.

Specifically, the present invention relates to the process for preparing the cyclohexane hexacarboxylic-1,2,4,5-diimide derivative which comprises reacting a bicyclooctene-1,2,4,5-tetracarboxylic anhydride with alkylamine and aniline derivative and then oxidizing the resulting product with ozone, potassium permanganate, ruthenium chloride hydroxide and hydrogen peroxide under non-basic conditions to convert the double bond into a dicarboxylic acid or a dialdehyde without destroying the imide group.

The present invention will be explained in detail in the following description.

The cyclohexane-1,2,4,5-diimide of the present invention can be represented by the formula I

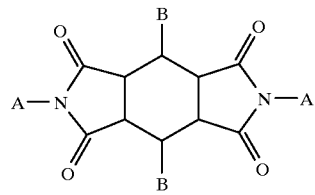
(I)

in which

A is —$R_1$—Z—X in which $R_1$ is optionally present or $R_1$ is $C_0$–$C_{30}$ alkyl or aralkyl or phenyl, Z is optionally present or is $CH_2$, S, O or NH, X is $CH_3$, $OR_3$, $SR_3$, $NO_2$, halogen, $CON(R_3)_2$, $COOR_3$ ($R_3$ is H or $C_1$–$C_{10}$ alkyl, aralkyl or phenyl) or COOM (M is alkali metal), B is $R_2$—Y in which $R_2$ is optionally present or $R_2$ is $C_0$–$C_{10}$ alkyl or aralkyl or phenyl, Y is COX' (X' is halogen), $CON(R_4)_2$, CHO, $COSR_4$, $CONHNH_2$, $C(CH_2)_2OH$, $CH_2OR_4$, $COOR_4$ ($R_4$ is H or $C_1$–$C_{10}$ alkyl) or COOM (M is alkali metal).

The present invention also relates to a process for preparing the cyclohexanediimide derivative of the formula I which comprises the steps of:

i) reacting the bicyclooctenetetracarboxylic dianhydride of the formula II

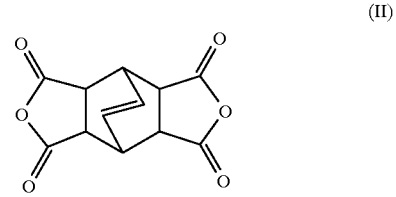
(II)

with the alkylamine or aniline derivative of formula A—$NH_2$ (III) to give a bicyclooctenetetracarboxylic diimide derivative of formula IV

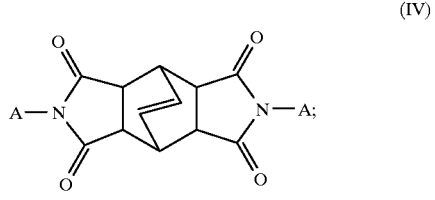
(IV)

ii) oxidizing the bicyclooctenetetracarboxylic diimide derivative of the formula. IV with ozone to give a compound of formula V

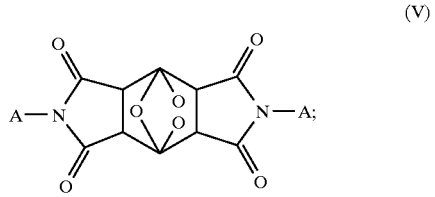
(V)

iii) secondarily oxidizing the compound of the formula V with aqueous hydrogen peroxide to give a compound of formula VI

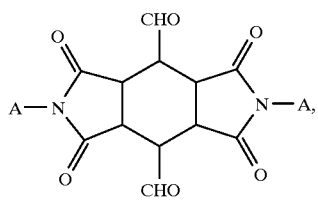

(VI)

iv) tertiarily oxidizing the compound of the formula VI with potassium permanganate to give a cyclohexanehexacarboxylic diimide of formula VII

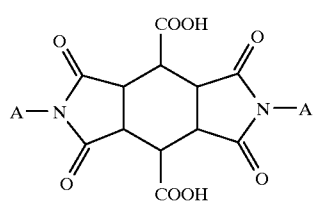

(VII)

(the first process).

The present invention relates to another process for preparing the cyclohexanehexacarboxylic diimide of the formula VII, which comprises oxidizing the compound of the formula IV with ruthenium chloride hydroxide and sodium periodate or sodium perchloride to give the compound of the formula VII (the second process).

The present invention also includes a process for preparing the cyclohexanehexacarboxylic diimide of the formula VII, which comprises reacting compound of the formula IV with ozone to give the compound of the formula V and then preparing the: compound of the formula VII by using Jone's reagent (the third process).

The Jone's reagent is $H_2CrO_4$ (0.267 mol $CrO_3$+0.451 mol $H_2SO_4$ in 100 ml of $H_2O$).

The present invention also includes a process for preparing the cyclohexanehexacarboxylic diimide of the formula VII, which comprises reacting compound of formula IV and then preparing the compound of the formula VII by using $H_2O_2$ in Formic acid (the fourth process).

The above-mentioned processes will be described in more detail in the following.

In the first process, the bicyclooctenetetracarboxylic dianhydride of the formula II is reacted with alkylamine, aromatic amine, or aromatic alkylamine of the formula III to give the bicyclooctenetetracarboxylic diimide derivative. The reaction of the bicyclooctenetetracarboxylic dianhydride of the formula II with alkylamine, aromatic amine, or aromatic alklamine of the formula III can be carried out by heating them in accordance with the known method to give the corresponding bicyclooctene tetracarboxylic diimide compound. The temperature used in this step is generally about 100 to about 200° C. Subsequently, the resulting bicyclooctene tetracarboxylic diimide derivative of the formula IV is reacted with ozone to give the compound of the formula V. Such ozonization reaction is carried out in an organic solvent such as acetone, methylene chloride, chloroform, or carbon tetrachloride. As a catalyst, pyridine is used. The resulting cyclohexane-3,6-diozonide-1,2,4,5-tetracarboxylic diimide of the formula V is reacted with aqueous hydrogen peroxide to give the cyclohexane-3,6-dialydehyde-1,2,4,5-tetracarboxylic diimide compound of the formula VI. As a solvent, acetone, methylene chloride, chloroform, or carbon tetrachloride can be used. The reaction temperature is from about 0 to about 100° C. Thus, the obtained compound of the formula VI is oxidized with potassium permanganate to give the compound of the formula VII as one of the end products and its derivatives. The solvent used in the reaction is a mixed solution of distilled water and pyridine, and the reaction temperature is from about 0 to about 100° C.

In the second process, the bicyclooctenetetracarboxylic diimide derivative of the formula IV is prepared by the same method as in the first process, and then the compound of the formula IV is oxidized with ruthenium chloride hydroxide and sodium periodate or sodium perchloride to give the compound of the formula VII as one of the end products. The solvent used in the reaction is either a mixed solution of acetonitrile, distilled water and pyridine, or an organic solvent such as acetone. The reaction temperature is from about 0 to about 70° C.

In the third process, after preparing the compound of the Formula IV by the same method as in the first process, the compound of the formula IV is reacted with ozone in a solvent such as acetone, methylene chloride, chloroform, or carbon tetrachloride. The reaction temperature is from about −80 to about 50° C. Subsequently, the resulting product is reacted with an excessive amount of Jone's reagent in acetone solvent at a temperature range of about −10 to about 40° C. for about 1 to about 3 days, and then extracted with ethyl acetate to give a final product, which is the compound of the formula VII and its derivatives.

"The cyclohexane hexacarboxylic-1,2,4,5-diimide derivative" of the formula VII can be prepared by another process (the fourth process. The fourth process will be described in detail in the following.

After preparing the compound of the formula IV by the same method as in the first process, the compound of the formula IV is reacted with ozone in a solvent such as acetone, methylene chloride, chloroform, or carbon tetrachloride. The reaction temperature is from about −80 to about 50° C. Subsequently, the solvent of this solution is removed from the reactor. After that, the residual solids are dissolved in formic acid; and hydrogen peroxide is added. The resulting solution is heated (e.g., to a temperature range of about 70 to about 80° C.) for several hours (e.g.,about 12 hours) to generate heat of reaction. The white crystals (compound VII) that are generated are collected and dried.

The above-mentioned compound of the formula VII can be reacted with a halide compound, an alkyl or aralkylalchol, or an amine at a temperature range from about 0 to about 200° C. to give the compound of the formula I in which B is COX' (X' is halogen), $COOR_4$, CHO, $COSR_4$, $CONHNH_2$, $CON(R_4)_2$ ($R_4$ is H or $C_1$–$C_{10}$ alkyl), $C(CH_2)_2OH$ or COOM (M is alkali metal).

The methods for making derivatives of formula I in which B is COX', $COOR_4$, $CONHNH_2$, $CON(R_4)_2$, $C(CH_2)_2OH$ or COOM are described below. Derivatives in which B is COX' are mentioned in example 11 (wherein, X' is chloride). And we can obtain derivatives in which B is $COOR_4$ from the reaction of COX' with alcohol (for example, methanol, ethanol, etc.). We can obtain derivatives in which B is $CONHNH_2$ from the reaction of COX' with hydrazine ($H_2NNH_2$), and we can obtain derivatives in which B is $CON(R_4)_2$ from the reaction of COX' with tert-alkylamine. Derivatives in which B is $C(CH_2)_2OH$ can be obtained from the reaction of COX' and a Grignard reagent ($R_4MgX'$, X' is Cl, Br, I). And derivatives in which B is COOM can be obtained from the reaction of COOH and alkaline salts such as KOH (in here, K is M.).

Derivatives in which B is $CH_2OR_4$ can be produced by the reduction of COOH in the compound of Formula VII. The COOH group of the compound of formula VII is reacted with $H_2O$ or $R_4OH$ catalyzed by $LiAlH_4$ and $H_2SO_4$.

The typical examples of cyclohexanehexacarboxylic-1,2,4,5-diimide derivative of formula I are as follows:

N,N-diphenylcyclohexane hexacarboxylic-1,2,4,5-diimide, N,N-diphenylcyclohexanehexacarboxylic-3,6-dichloride-1,2,4,5-diimide, N,N-bis(p-hydroxyphenyl) cyclohexane hexacarboxylic-1,2,4,5-diimide, N,N-bis(p-thiolphenyl)cyclohexane hexacarboxylic-1,2,4,5-diimide, N,N-bis(p-bromophenyl)cyclohexane hexacarboxylic-1,2,4,5-diimide, N,N-bis(p-iodophenyl)cyclohexane hexacarboxylic-1,2,4,5-diimide, N,N-bis(p-chlorophenyl)cyclohexanehexacarboxylic-1,2,4,5-diimide, N,N-bis(p-aldehyde)cyclohexane hexacarboxylic-1,2,4,5-diimide, N,N-bis (p-cyanophenyl)cyclohexane hexacarboxylic-1,2,4,5-diimide, N,N-bis(p-carboxylic acid ester phenyl) cyclohexane hexacarboxylic-1,2,4,5-diimide, N,N-bis(p-carboxylic acid phenyl) cyclohexane hexacarboxylic-1,2,4,5-diimide, N,N-dibenzylcyclohexane hexacarboxylic-1,2,4,5-diimide, N,N-bis(p-sulfonic acid phenyl)cyclohexane hexacarboxylic-1,2,4,5-diimide, di(bromomethyl) cyclohexane hexacarboxylic-1,2,4,5-diimide, N,N-di(chloromethyl)cyclohexane hexacarboxylic-1,2,4,5-diimide, N,N-di(iodomethyl)cyclohexane hexacarboxylic-1,2,4,5-diimide, N,N-di(hydroxymethyl)cyclohexane hexacarboxylic-1,2,4,5-diimide, N,N-di(thiolmethyl) cyclohexane hexacarboxylic-1,2,4,5-diimide, N,N-di(cyanomethyl)cyclohexane hexacarboxylic-1,2,4,5-diimide, N,N-di(sulfonic acid methyl)cyclohexane hexacarboxylic-1,2,4,5-diimide, N,N-di(carboxylic acid methyl)cyclohexane hexacarboxylic-1,2,4,5-diimide, N,N-di(carboxylic acid ester methyl)cyclohexane hexacarboxylic-1,2,4,5-diimide, N,N-diphenylcyclohexane-3,6-dialdehyde-1,2,4,5-tetracarboxylic diimide, N,N-diphenyl cyclohexane-3,6-dichloride-1,2,4,5-diimide, N,N-bis(p-hydroxyphenyl) cyclohexane-3,6-dialdehyde-1,2,4,5-tetracarboxylic diimide, N,N-bis (p-thiolphenyl)cyclohexane-3,6-dialdehyde-1,2,4,5-tetracarboxylic diimide, N,N-bis(p-bromophenyl)cyclohexane-3,6-dialdehyde-1,2,4,5-tetracarboxylic diimide, N,N-bis(p-iodophenyl) cyclohexane-3,6-dialdehyde-1,2,4,5-tetracarboxylic diimide, N,N-bis(p-chlorophenyl)cyclohexane-3,6-dialdehyde-1,2,4,5-tetracarboxylic diimide, N,N-bis(p-aldehydephenyl)cyclohexane-3,6-1,2,4,5-tetracarboxylic diimide, N,N-bis(p-cyanophenyl)cyclohexane-3,6-dialdehyde-1,2,4,5-tetracarboxylic diimide, N,N-bis(p-carboxylic acid ester phenyl)cyclohexane-3,6-dialdehyde-1,2,4,5-tetracarboxylic diimide, N,N-bis(p-carboxylic acid phenyl) cyclohexane-3,6-dialdehyde-1,2,4,5-tetracarboxylic diimide, N,N-dibenzylcyclohexane-3,6-dialdehyde-1,2,4,5-tetracarboxylic diimide, N,N-bis(p-sulfonic acid phenyl) cyclohexane-3,6-dialdehyde-1,2,4,5-tetracarboxylic diimide, N,N-di(bromomethyl)cyclohexane-3,6-dialdehyde-1,2,4,5-tetracarboxylic diimide, N,N-di(chloromethyl) cyclohexane-3,6-dialdehyde-1,2,4,5-tetracarboxylic diimide, N,N-di(iodomethyl)cyclohexane-3,6-dialdehyde-1,2,4,5-tetracarboxylic diimide, N,N-di(hydroxymethyl) cyclohexane-3,6-dialdehyde-1,2,4,5-tetracarboxylic diimide, N,N-di(thiolmethyl)cyclohexane-3,6-dialdehyde-1,2,4,5-tetracarboxylic diimide, N,N-di(cyanomethyl) cyclohexane-3,6-dialdehyde-1,2,4,5-tetracarboxylic diimide, N,N-di(sulfonic acid methyl)cyclohexane-3,6-dialdehyde-1,2,4,5-tetracarboxylic diimide, N,N-di(carboxylic acid methyl)cyclohexane-3,6-dialdehyde-1,2,4,5-tetracarboxylic diimide, N,N-diphenyl cyclohexane-3,6-dinitro-1,2,4,5-tetracarboxylic diimide, N,N-diphenylcyclohexane hexacarboxylic acid-3,6-dichloride-1,2,4,5-tetracarboxylic diimide, N,N-bis(p-hydroxylphenyl) cyclohexane-3,6-dinitro-1,2,4,5-tetracarboxylic diimide, N,N-bis(p-thiolphenyl) cyclohexane-3,6-dinitro-1,2,4,5-tetracarboxylic diimide, N,N-bis(p-bromophenyl) cyclohexane-3,6-dinitro-1,2,4,5-tetracarboxylic diimide, N,N-bis(p-iodophenyl)cyclohexane-3,6-dinitro-1,2,4,5-tetracarboxylic diimide, N,N-bis(p-chlorophenyl) cyclohexane-3,6-dinitro-1,2,4,5-tetracarboxylic diimide, N,N-bis(p-aldehydephenyl) cyclohexane-3,6-dinitro-1,2,4,5-tetracarboxylic diimide, N,N-bis(p-cyanophenyl) cyclohexane-3,6-dinitro-1,2,4,5-tetracarboxylic diimide, N,N-bis(p-carboxylic acid ester phenyl)cyclohexane-3,6-dinitro-1,2,4,5-tetracarboxylic diimide, N,N-bis(p-carboxylic acid phenyl)cyclohexane-3,6-dinitro-1,2,4,5-tetracarboxylic diimide, N,N-dibenzylcyclohexane-3,6-dinitro-1,2,4,5-tetracarboxylic diimide, N,N-bis(p-sulfonic acid phenyl)cyclohexane-3,6-dinitro-1,2,4,5-tetracarboxylic diimide, N,N-di(bromomethyl)cyclohexane-3,6-dinitro-1,2,4,5-tetracarboxylic diimide, N,N-di(chloromethyl) cyclohexane-3,6-dinitro-1,2,4,5-tetracarboxylic diimide, N,N-di(iodomethyl)cyclohexane-3,6-dinitro-1,2,4,5-tetracarboxylic diimide, N,N-di(hydroxymethyl) cyclohexane-3,6-dinitro-1,2,4,5-tetracarboxylic diimide, N,N-di(thiolmethyl)cyclohexane-3,6-dinitro-1,2,4,5-tetracarboxylic diimide, N,N-di(cyanomethyl) cyclohexane-3,6-dinitro-1,2,4,5-tetracarboxylic diimide, N,N-di(sulfonic acid methyl)cyclohexane-3,6-dinitro-1,2,4,5-tetracarboxylic diimide, N,N-di(carboxylic acid ethyl) cyclohexane-3,6-dinitro-1,2,4,5-tetracarboxylic diimide, N,N-di(carboxylic acid ester methyl)cyclohexane-3,6-dinitro-1,2,4,5-tetracarboxylic diimide, N,N-di(carboxylic acid ester methyl) cyclohexane-3,6-dialdehyde-1,2,4,5-tetracarboxylic diimide, N,N-diphenylcyclohexane hexacarboxylic-3,6-dichloride-1,2,4,5-imide.

The present invention will now be explained in more detail with reference to the following examples, but it is to be understood that the present invention is not restricted thereto and various modifications are possible within the scope of the invention.

EXAMPLE 1

50 g (0.201 mole) of the bicyclooctenetetracarboxylic dianhydride was introduced in a 500 ml round flask and 250 ml of purified dimethyl acetamide was poured with stirring and they were dissolved by heating them up to 100° C. When all the reactants in the flask were dissolved, 37 ml (0.41 mole) of aniline and 20 ml of purified toluene were added and then reacted at 125° C. for 4 hours while the formed water was removed with toluene by azeotropic distillation. 98% of N,N'-bis(phenyl)bicyclooct[2.2.2]ene-1,2,4,5-tetracarboxylic diimide (hereinafter, referred to as "BCODI") was obtained by separating the product from the reaction solution.

10 g of BCODI (IV) was introduced in 2 liter flask, and then 800 ml of methylene chloride was poured with sufficient stirring. When BCODI (IV) was completely dissolved, the reactor was soaked in a mixture solution of dry ice and acetone and the inner temperature of reactor was cooled to −78° C. While maintaining −78° C., oxygen and ozone through an inlet tube where dispersion is well carried out were injected to the reactor. The injected amounts of oxygen and ozone were 100 liter/hr and 4.6 g/hr, respectively. After they were reacted for 2 hours, whether or not BCODI (IV) remained was confirmed by thin layer chromatography. The reaction was stopped when no BCODI (IV) was found. After the reaction, nitrogen was passed through the reactor to remove the remaining ozone. 20 ml of 35% by weight of aqueous hydrogen peroxide was injected while keeping the temperature of the reactants to 0° C. and was stirred for 1 hour. Again, the temperature was maintained at a room temperature while stirring for 24 hours. The resulting solid product was recovered and washed with distilled water 3 to 4 times, and with methylene chloride 3 to 4 times. The solid product was dried in a vacuum oven at 30° C. for 24 hours to yield N,N-diphenylcyclohexane-3,6-dialdehyde-1,2,4,5-tetracarboxylicdiimide (VI) (hereinafter referred to as "PHALDI").

EXAMPLE 2

10 g of BCODI (IV) was introduced in a 2 liter flask, and then 1000 ml of acetone was poured with sufficient stirring. When BCODI (IV) was completely dissolved, the reactor was soaked in a mixture solution of dry ice and acetone and the inner temperature of reactor was cooled to −78° C. While maintaining −78° C., oxygen and ozone through an inlet tube where dispersion is well carried out were injected to the reactor. The injected amounts of oxygen and ozone were 100 liter/hr and 4.6 g/hr, respectively. After they were reacted for 2 hours, whether or not BCODI (IV) remained was confirmed by thin layer chromatography. The reaction was stopped when no BCODI (IV) was found. After the reaction, nitrogen was passed through a reactor to remove the remaining ozone. The acetone solvent of reactant was removed under reduced pressure at 45° C. and completely dissolved the solid product by pouring 50 ml of formic acid. 35 ml of 35% aqueous hydrogen peroxide solution was poured into the solution and they were reacted at 70° C. for 12 hours. The resulting precipitate was recovered and washed with ethyl acetate 3 to 4 times, and was separated in dimethyl acetate amide solvent. The removed precipitate was dried in a vacuum oven at 30° C. for 24 hours to yield N,N-diphenylcyclohexane carboxylic-1,2,4,5-diimide (VII) (hereinafter referred to as "PHHCDI").

EXAMPLE 3

10 g of PHALDI (VI) (m.p. 213.8° C.) synthesized in Example 1 and 200 ml of pyridine were added respectively in a 500 ml flask and were heated to 50° C. After PHALDI (VI) was completely dissolved, 100 ml of distilled water and 10 g of potassium permanganate were added and they were reacted for 24 hours while heated to 80° C. After the reaction, manganese oxide was filtered by using a celite pad and the solvent of filtered solution was completely removed under reduced pressure. To the remaining solid was added 50 ml of distilled water to completely dissolve the solid. To this solution was added 5 N hydrochloric acid in a series of small portions to adjust pH to 3. The precipitate was occurred. The resulting precipitate was recovered and isolated after being dissolved in acetone. The solid product was dried in a vacuum oven at 30° C. for 24 hours to yield PHHCDI (VII).

EXAMPLE 4

7 g of BCODI (IV) was introduced in a 1 liter flask, and then 150 ml of methylene chloride and 250 ml of acetonitrile were poured with sufficient stirring for a complete dissolution. 200 ml of distilled water and 10 g of sodium periodate were dissolved in another beaker and the mixture was introduced slowly into the reaction flask. 0.08 g of ruthenium chloride hydroxide was added in a series of small portions while stirring the reaction mixture vigorously and then they were reacted at a room temperature for 48 hours. The resulting precipitate having a black color was removed. The aqueous solution of supernatant was evaporated until 50 ml was remained and then 100 ml of acetone was poured to the solution. After sodium periodate which was precipitated as a crystal due to acetone was filtered, the remaining acetone in the solution was removed under reduced pressure. To the 50 ml of final aqueous solution was added 5 N hydrochloric acid in dropwise to adjust pH to 3. The resulting precipitate was dissolved in acetone and was separated. The solid was dried in a vacuum oven at: 30° C. for 24 hours to yield PHHCDI (VII).

EXAMPLE 5

7 g of BCODI (IV) was introduced in a 1 liter flask, and then 150 ml of methylene chloride and 250 ml of acetonitrile were poured with sufficient stirring for a complete dissolution. 200 ml of distilled water and 15 ml of sodium hyperchloride were poured into an(other beaker and the mixture was introduced slowly into the flask. 0.08 g of ruthenium chloride hydroxide was added in a series of small portions while stirring the reaction mixture vigorously and then they were reacted at a room temperature for 48 hours. The resulting precipitate having a black color was removed. The aqueous solution of supernatant was evaporated until 50 ml was remained and then 100 ml of acetone was poured to the solution. After removing acetone from the remaining solution of the supernatant under reduced pressure, 5 N hydrochloric acid was added in dropwise to approximately 50 ml of final aqeous solution to adjust pH to 3. The resulting precipitate was dissolved in acetone and was separated. The solid was dried in a vacuum oven at 30° C. for 24 hours to yield PHHCDI (VII).

EXAMPLE 6

10 g of BCODI (IV) was introduced in 2 liter flask, and then 1,100 ml of acetone was poured with sufficient stirring. When BCODI (IV) was completely dissolved, the reactor was soaked in a mixture solution of dry ice and acetone and the inner temperature of the reactor was cooled to −78° C. While maintaining −78° C., oxygen and ozone were injected to the reactor through an inlet tube where dispersion is well carried out. The injected amounts of oxygen and ozone were 100 liter/hr and 4.6 g/hr, respectively. After they were reacted for 2 hours, whether or not BCODI (IV) remained was confirmed by thin layer chromatography. The reaction was stopped when no BCODI (IV) was found. After the reaction, nitrogen was passed through a reactor to remove the remaining ozone. While the temperature of the reactant was maintained at 0° C., 48 ml of Jone's reagent was injected and stirred vigorously for 1 hour. Under the condition that room temperature was maintained, the reactant was stirred for 3 days. After the reaction was completed, the resulting chromium salt: was removed and acetone in the remaining solution was removed under reduced pressure. After removing acetone, the remaining solid was recovered and sufficiently dissolved in an excessive amount of ethyl acetate. 500 ml of ethyl acetate was removed from the solution and was subjected to an isolation at a low temperature to give PHHCDI (VII).

EXAMPLE 7

The procedure of Example 5 was repeated except that 50 ml of 5 N hydrochloric acid was added to the reaction solvent.

EXAMPLE 8

The procedure of Example 5 was repeated except that the reaction temperature was 0° C. and the reaction time was 4 hours.

EXAMPLE 9

50 g (0.201 mole) of the bicyclooctenetetracarboxylic dianhydride was introduced in a 500 ml round flask and 250 ml of purified dimethyl acetamide was poured with stirring and they were dissolved by heating them up to 100° C. When all the reactants in the flask were dissolved, 71 g (0.40 mole) of sulfanilic acid and 20 ml of purified toluene were added and then reacted at 125° C. for 4 hours while the formed water was removed with toluene by azeotropic distillation. 96% of N,N'-bis(p-sulfonic acid phenyl)bicyclooct[2.2.2]ene-1,2,4,5-tetracarboxylic diimide (hereinafter referred to as "SBCODI") was obtained by separating the product from the reaction solution.

10 g of SBCODI was introduced in a 2 liter flask, and then 1000 ml of acetone was poured with sufficient stirring. When SBCODI was completely dissolved, the reactor was soaked in a mixture solution of dry ice and acetone and the inner temperature of the reactor was cooled to −78° C. While maintaining −78° C., oxygen and ozone was injected to the reactor through an inlet tube where dispersion is well carried out. The injected amounts of oxygen and ozone were 100 liter/hr and 4.6 g/hr, respectively. After they were reacted for 3 hours, whether or not SBCODI remained was confirmed by thin layer chromatography. The reaction was stopped when no SBCODI was found. After the reaction, nitrogen was passed through a reactor to remove the remaining ozone. Under reduced pressure at 45° C., all the acetone solvent in the reactants was removed and 50 ml of formic acid was poured to dissolve all solid. 35 ml of 35% aqueous hydrogen peroxide solution was poured to the solution and they were reacted at 70° C. for 12 hours. The resulting precipitate was recovered and washed with ethyl acetate 3 to 4 times. After the separation from dimethyl acetamide solvent, the solid product was dried in a vacuum oven at 30° C. for 24 hours to yield N,N'-bis(p-sulfonic acid phenyl)cyclohexane hexacarboxylic-1,2,4,5-diimide (hereinafter, referred to as "SHCDI").

EXAMPLE 10

50 g (0.201 mole) of the bicyclooctenetetracarboxylic dianhydride was introduced in a 500 ml round flask and 250 ml of purified dimethyl acetamide was poured with stirring and they were dissolved by heating them up to 100° C. When all the reactants in the flask were dissolved, 28.47 ml (0.41 mole) of benzylamine and 20 ml of purified toluene were added and then they were reacted at 125° C. for 4 hours while the formed water was removed with toluene by azeotropic distillation. 94% of N,N'-bisbenzyl bicyclooct[2.2.2]ene-1,2,4,5-tetracarboxylic diimide (hereinafter referred to as "BZBCODI") was obtained by separating the product from the reaction solution.

10 g of BZBCODI was introduced in a 2 liter flask, and then 1000 ml of acetone was poured with sufficient stirring. When BZBCODI was completely dissolved, the reactor was soaked in a mixture solution of dry ice and acetone and the inner temperature of the reactor was cooled to −78° C. While maintaining −78° C., oxygen and ozone was injected to the reactor through an inlet tube where dispersion is well carried out. The injected amounts of oxygen and ozone were 100 liter/hr and 4.6 g/hr, respectively. After they were reacted for 3 hours, whether or not BZBCODI remained was confirmed by thin layer chromatography. The reaction was stopped when no BZBCODI was found. After the reaction, nitrogen was passed through the reactor to remove the remaining ozone. Under reduced pressure at 45° C., all the acetone solvent in the reactants was removed and 50 ml of formic acid was poured to dissolve all solid. To the solution was poured 35 ml of 35% aqueous hydrogen peroxide solution and they were reacted at 70° C. for 12 hours. The resulting precipitate was recovered and washed with ethyl acetate 3 to 4 times. After separation from dimethyl acetamide solvent, the solid product was dried in a vacuum oven at 30° C. for 24 hours to yield N,N'-bisbenzylcyclohexanehexacarboxylic-1,2,4,5-diimide (hereinafter referred to as "BZHCDI").

EXAMPLE 11

5 g of PHHCDI (VII) which was synthesized in Example 2 was added to a 100 ml round flask and 50 ml of dichloro sulfoxide ($SOCl_2$) was introduced. Under nitrogen atmosphere, the mixture was refluxed at −79° C. for 48 hours. After the reaction was completed, the reactor was left at −10° C. for a day. The precipitate of the product, N,N-diphenylcyclohexane hexacarboxylic-3,6-diacid chloride-1,2,4,5-diimide (hereinafter referred to as "PHHCDICl") was washed with cold dichloro sulfoxide solution for several times and then dissolved again in dichloro sulfoxide. The dissolved solution was dried in a vacuum oven at 80° C. to give PHHCDICl.

Table 1 below shows the reaction condition and the yield of the product prepared in the Examples.

TABLE 1

| Example | Product | Oxidizing agent | Reaction condition 1st reaction/2nd reaction | Yield (%) | Comparison |
|---|---|---|---|---|---|
| 1 | PHALDI | $O_3$ | MC, −78° C., | 35 | |
|   | PHOZDI | $H_2O_2$ | 2 hr//24 hr | 65 | |
| 2 | PHHCDI | $O_3$ | Acetone, −78° 2 hr// | 72 | |
|   |   | $H_2O_2$ | HCOOH, $H_2O_2$, 75° C. |   | |
| 3 | PHHCDI | $KMnO_4$ | Pyridine, $H_2O$, 100° C.// | 70 | Reactant: |
|   |   |   | 24 hr |   | CHALDI |
| 4 | PHHCDI | $RuCl_3 \times H_2O$/ | MC, Acetonitrile, $H_2O$// | 35 | |
|   |   | $NaIO_4$ | RT/48 hr |   | |
| 5 | PHHCDI | $RuCl_3 \times H_2O$/ | MC, Acetonitrile, $H_2O$// | 50 | |
|   |   | NaOCl/HCl | RT/48 hr |   | |
| 6 | PHHCDI | $O_3$ | Acetone, −78° C. 2 hr | 68 | |
|   | PHOZDI | Jone's reagent |   | 20 | |
| 7 | PHHCDI | $O_3$ | Acetone, −78° C., 2 hr | 81 | Add HCl in |
|   | PHOZDI | Jone's reagent |   | 15 | second reaction |
| 8 | PHHCDI | $O_3$ | Acetone, −78° C., 2 hr | 50 | Add HCl in |
|   |   | Jone's reagent |   |   | second reaction |

TABLE 1-continued

| Example | Product | Oxidizing agent | Reaction condition 1st reaction/2nd reaction | Yield (%) | Comparison |
|---|---|---|---|---|---|
| 9 | SHCDI | $O_3$ $H_2O_2$ | Acetone, −78° C., 3 hr// HCOOH, $H_2O_2$, 75° C. | 55 | |
| 10 | BZHCDI | $O_3$ $H_2O_2$ | Acetone, −78° C., 3 hr// HCOOH, $H_2O_2$, 75° C. | 60 | |
| 11 | PHHCDICI | | $SOCl_2$, 80° C. $N_2$ atmosphere | 82 | |

PHOZDI (V): N,N-diphenylcyclohexane-3,6-diozonide-1,2,4,5-tetracarboxylic diimide PHALDI (VI): N,N-diphenylcyclohexane-3,6-dialdehyde-1,2,4,5-tetracarboxylic diimide PHHCDI (VII): N,N-diphenylcyclohexanecarboxylic-1,2,4,5-diimide SHCDI: N,N'-bis(p-sulfonic acid phenyl)cyclohexanehexacarboxylic-1,2,4,5-diimide BZHCDI: N,N'-bisbenzylcyclohexanecarboxylic-1,2,4,5-diimide PHHCDICI: N,N'-diphenylcyclohexanehexacarboxylic-3,6-diacid chloride-1,2,4,5-diimide.

What is claimed is:

1. A cyclohexane-1,2,4,5-diimide derivative of formula I:

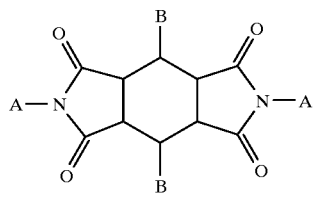

(I)

in which

A is —$R_1$—Z—X in which $R_1$ is $C_0$–$C_{30}$ alkyl or aralkyl or phenyl,

Z is optionally present or is $CH_2$, S, O or NH,

X is $CH_3$, $OR_3$, $SR_3$, $NO_2$, halogen, $CON(R_3)_2$, $COOR_3$, or COOM, wherein $R_3$ is H or $C_1$–$C_{10}$ alkyl, aralkyl or phenyl and wherein M is alkali metal; and B is —$R_2$—Y in which $R_2$ is $C_0$–$C_{10}$ alkyl or aralkyl or phenyl, Y is COX', $CON(R_4)_2$, CHO, $COSR_4$, $CONHNH_2$, $C(CH_2)_2OH$, $CH_2OR_4$, COOH, or COOM, wherein X' is halogen, $R_4$ is H or $C_1$–$C_{10}$ alkyl, and M is alkali metal.

2. A cyclohexane-1,2,4,5-diimide derivative of formula VII

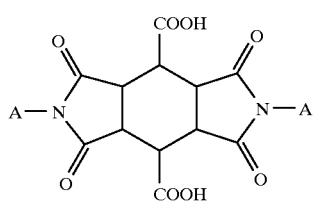

(VII)

in which A is —$R_1$—Z—X in which $R_1$ is $C_0$–$C_{30}$ alkyl or aralkyl or phenyl, Z is optionally present or is CH, S, O or NH, X is $CH_3$, $OR_3$ $SR_3$, $NO_2$, halogen, $COOR_3$, or COOM, wherein $R_3$ is H or $C_1$–$C_{10}$ alkyl, aralkyl or phenyl and wherein M is alkali metal.

3. A process for preparing a cyclohexane hexacarboxylic-1,2,4,5-diimide derivative of formula VII,

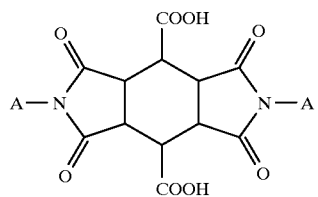

(VII)

the process comprising the steps of:

i) reacting a bicyclooctenetetracarboxylic dianhydride of formula II

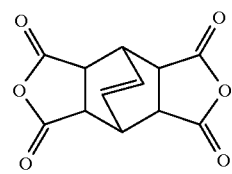

(II)

with an alkylamine or aniline derivative of formula A—$NH_2$ to yield a bicyclooctenetetracarboxylic diimide derivative of formula IV

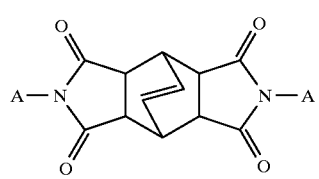

(IV)

ii) reacting the bicyclooctenetetracarboxylic diimide derivative of formula IV with about 2 to about 6 g/hr of ozone per 25 mmol of the derivative of formula IV in an acetone or a methylene chloride solvent at a temperature range from about −80° C. to about 30° C. to yield a resulting product and then reacting the resulting product with about 1 to about 10,000% by weight of about 35% aqueous hydrogen peroxide solution in the presence of about 100% to about 10,000% by weight of formic acid to yield a cyclohexane hexacarboxylic-1,2,4,5-diimide derivative of formula VII, wherein A is —$R_1$—Z—X in which $R_1$ is $C_0$–$C_{30}$ alkyl or aralkyl or phenyl, Z is optionally present or is CH$_2$, S, O or NH, and X is CH$_3$, OR$_3$, SR$_3$, NO$_2$, halogen, CON(R$_3$)$_2$, COOR$_3$ or COOM, wherein R$_3$ is H or C$_1$–C$_{10}$ alkyl, aralkyl or phenyl and wherein M is alkali metal.

4. A process for preparing a cyclohexane hexacarboxylic-1,2,4,5-diimide derivative of formula VII

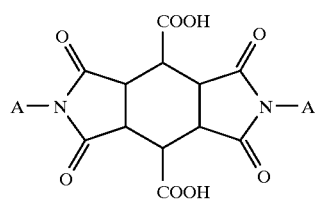

(VII)

as claimed in claim 2, the process comprising the steps of:

i) reacting a bicyclooctenetetracarboxylic dianhydride of formula II

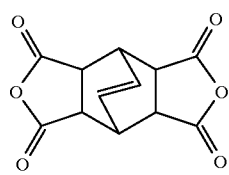

(II)

with an alkylamine or aniline derivative of formula A—NH$_2$ to yield a bicyclooctenetetracarboxylic diimide derivative of formula IV

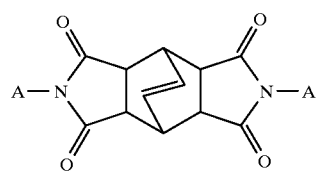

(IV)

ii) reacting the bicyclooctenetetracarboxylic diimide derivative of formula IV with about 2 to about 6 g/hr of ozone per 25 mmol of the derivative of formula IV in an acetone or a methylene chloride solvent at a temperature range from about –80° C. to about 30° C. to yield a resulting product and then reacting the resulting product with about 1% to about 100% by weight of Jone's reagent to yield a cyclohexanehexacarboxylic-1,2,4,5-diimide derivative of formula VII wherein A is —R$_1$—Z—X in which R$_1$ is C$_0$—C$_{30}$ alkyl or aralkyl or phenyl, Z is optionally present or is CH$_2$, S, O or NH, and X is CH$_3$, OR$_3$, SR$_3$, NO$_2$, halogen, CON(R$_3$)$_2$, COOR$_3$ or COOM, wherein R$_3$ is H or C$_1$–C$_{10}$ alkyl, aralkyl or phenyl and wherein M is alkali metal.

5. A process for preparing a cyclohexane-3,6-dialdehyde-1,2,4,5-diimide derivative of formula I

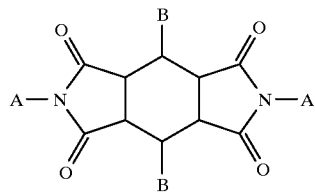

(I [VI])

as claimed in claim 1, wherein B is CHO and wherein A is —R$_1$—Z—X in which R$_1$ is C$_0$–C$_{30}$ alkyl or aralkyl or phenyl, Z is optionally present or is CH$_2$, S, O or NH, and X is CH$_3$, OR$_3$, SR$_3$, NO$_2$, halogen, CON(R$_3$)$_2$, COOR$_3$ or COOM, wherein R$_3$ is H or C$_1$–C$_{10}$ alkyl, aralkyl or phenyl and wherein M is alkali metal, the process comprising the steps of:

reacting a derivative of formula IV

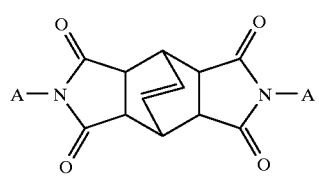

(IV)

with about 2 to about 6 g/hr of ozone per 25 mmol of the derivative of formula IV in a methylene chloride solvent at a temperature range from about –80° C. to about 30° C. to yield a resulting product and then reacting the resulting product with about 1% to about 10,000% by weight of about 35% aqueous hydrogen peroxide.

6. A process according to claim 3 wherein the derivative of formula VII is reacted with a halide compound, an alkyl or aralkyl alcohol, or an amine at a temperature range from about 0° C. to about 200° C. to yield a cyclohexane-1,2,4,5-diimide derivative of formula I

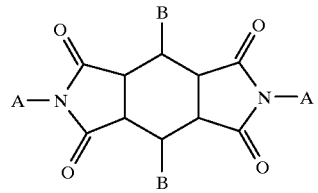

(I)

wherein A is —R$_1$—Z—X in which R$_1$ is C$_0$–C$_{30}$ alkyl or aralkyl or phenyl, Z is optionally present or is CH$_2$, S, O or NH, X is CH$_3$, OR$_3$, SR$_3$, NO$_2$, halogen, CON(R$_3$)$_2$, COOR$_3$ or COOM, wherein R$_3$ is H or C$_1$–C$_{10}$ alkyl, aralkyl or phenyl and wherein M is alkali metal; and B is COX', CHO, COSR$_4$, CONHNH$_2$, CON(R$_4$)$_2$, C(CH$_2$)$_2$OH, or COOM, wherein X' is halogen, R$_4$ is H or C$_1$–C$_{10}$ alkyl, and M is alkali metal.

7. A process for preparing a cyclohexane-1,2,4,5-diimide derivative as claimed in claim 1, the process comprising:

reacting a cyclohexane-3,6-dialdehyde-1,2,4,5-diimide derivative with about 1 to about 1,000% by weight of potassium permanganate (KMnO$_4$) at a temperature range from about 0 to about 110° C. in a mixture of pyridine and water.

8. A process for preparing a cyclohexane-1,2,4,5-diimide derivative of formula I

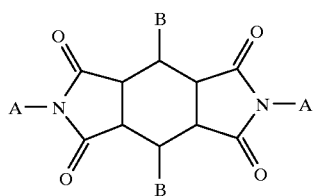

(I)

the process comprising reacting a derivative of formula VII

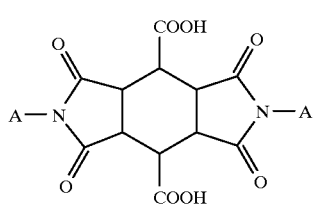

(VII)

as claimed in claim 1 with a halide compound, an alkyl or aralkyl alcohol, or an amine at a temperature range from about 0° C. to about 200° C. to yield the cyclohexane-1,2,4,5-diimide derivative of formula I,
wherein A is —R$_1$—Z—X in which R$_1$ is C$_0$–C$_{30}$ alkyl or aralkyl or phenyl, Z is optionally present or is CH$_2$, S, O or NH, X is CH$_3$, OR$_3$, SR$_3$, NO$_2$, halogen, CON(R$_3$)$_2$, COOR$_3$ or COOM,
wherein R$_3$ is H or C$_1$–C$_{10}$ alkyl, aralkyl or phenyl and wherein M is alkali metal; and B is COX', CHO, COSR$_4$ CONHNH$_2$, CON(R$_4$)$_2$, C(CH$_2$)$_2$OH, or COOM,
wherein X' is halogen, R$_4$ is H or C$_1$–Cl$_{10}$ alkyl, and M is alkali metal.

9. A cyclohexane-1,2,4,5-diimide derivative of formula I as claimed in claim 1, wherein Y is COX', CHO, COSR$_4$, CONHNH$_2$, or C(CH$_2$)$_2$OH,
wherein X' is halogen, and wherein R$_4$ is H or C$_3$–C$_{10}$ alkyl.

10. A cyclohexane-1,2,4,5-diimide derivative of formula I:

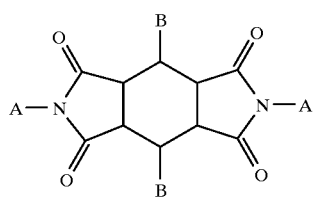

(I)

in which
A is —R$_1$—Z—X in which R$_1$ is C$_0$–C$_{30}$ alkyl or aralkyl or phenyl, Z is optionally present or is CH$_2$, S, O or NH, X is SR$_3$, NO$_2$, or halogen,
wherein R$_3$ is H or C$_1$–C$_{10}$ alkyl, aralkyl or phenyl; and B is —R$_2$—Y in which R$_2$ is C$_0$–C$_{10}$ alkyl or aralkyl or phenyl,
Y is COX', CON(R$_4$)$_2$, CHO, COSR$_4$, CONHNH$_2$, C(CH$_2$)$_2$OH, CH$_2$OR$_4$, COOR$_4$, or COOM,
wherein X' is halogen, R$_4$ is H or C$_1$–C$_{10}$ alkyl, and M is alkali metal.

11. A cyclohexane-1,2,4,5-diimide derivative selected from the group consisting of N,N-diphenylcyclohexane hexacarboxylic-1,2,4,5-diimide, N,N-diphenylcyclohexanehexacarboxylic-3,6-dichloride-1,2,4,5-diimide, N,N-bis(p-hydroxyphenyl)cyclohexane hexacarboxylic-1,2,4,5-diimide, N,N-bis(p-thiolphenyl) cyclohexane hexacarboxylic-1,2,4,5-diimide, N,N-bis(p-bromophenyl)cyclohexane hexacarboxylic-1,2,4,5-diimide, N,N-bis(p-iodophenyl)cyclohexane hexacarboxylic-1,2,4,5-diimide, N,N-bis(p-chlorophenyl) cyclohexanehexacarboxylic-1,2,4,5-diimide, N,N-bis(p-aldehyde)cyclohexane hexacarboxylic-1,2,4,5-diimide, N,N-bis(p-cyanophenyl)cyclohexane hexacarboxylic-1,2,4,5-diimide, N,N-bis(p-carboxylic acid ester phenyl) cyclohexane hexacarboxylic-1,2,4,5-diimide, N,N-bis(p-carboxylic acid phenyl)cyclohexane hexacarboxylic-1,2,4,5-diimide, N,N-dibenzylcyclohexane hexacarboxylic-1,2,4,5-diimide, N,N-bis(p-sulfonic acid phenyl)cyclohexane hexacarboxylic-1,2,4,5-diimide, N,N-di(bromomethyl) cyclohexane hexacarboxylic-1,2,4,5-diimide, N,N-di (chloromethyl)cyclohexane hexacarboxylic-1,2,4,5-diimide, N,N-di(iodomethyl)cyclohexane hexacarboxylic-1,2,4,5-diimide, N,N-di(hydroxymethyl)cyclohexane hexacarboxylic-1,2,4,5-diimide, N,N-di(thiolmethyl) cyclohexane hexacarboxylic-1,2,4,5-diimide, N,N-di (cyanomethyl)cyclohexane hexacarboxylic-1,2,4,5-diimide, N,N-di(sulfonic acid methyl)cyclohexane hexacarboxylic-1,2,4,5-diimide, N,N-di(carboxylic acid methyl)cyclohexane hexacarboxylic-1,2,4,5-diimide, N,N-di(carboxylic acid ester methyl)cyclohexane hexacarboxylic-1,2,4,5-diimide, N,N-diphenylcyclohexane-3,6-dialdehyde-1,2,4,5-tetracarboxylic diimide, N,N-diphenyl cyclohexane-3,6-dichloride-1,2,4,5-diimide, N,N-bis(p-hydroxyphenyl) cyclohexane-3,6-dialdehyde-1,2,4,5-tetracarboxylic diimide, N,N-bis(p-thiolphenyl)cyclohexane-3,6-dialdehyde-1,2,4,5-tetracarboxylic diimide, N,N-bis(p-bromophenyl)cyclohexane-3,6-dialdehyde-1,2,4,5-tetracarboxylic diimide, N,N-bis(p-iodophenyl) cyclohexane-3,6-dialdehyde-1,2,4,5-tetracarboxylic diimide, N,N-bis(p-chlorophenyl)cyclohexane-3,6-dialdehyde-1,2,4,5-tetracarboxylic diimide, N,N-bis(p-aldehydephenyl)cyclohexane-3,6-dialdehyde-1,2,4,5-tetracarboxylic diimide, N,N-bis(p-cyanophenyl) cyclohexane-3,6-dialdehyde-1,2,4,5-tetracarboxylic diimide, N,N-bis(p-carboxylic acid ester phenyl) cyclohexane-3,6-dialdehyde-1,2,4,5-tetracarboxylic diimide, N,N-bis(p-carboxylic acid phenyl) cyclohexane-3,6-dialdehyde-1,2,4,5-tetracarboxylic diimide, N,N-dibenzylcyclohexane-3,6-dialdehyde-1,2,4,5-tetracarboxylic diimide, N,N-bis(p-sulfonic acid phenyl) cyclohexane-3,6-dialdehyde-1,2,4,5-tetracarboxylic diimide, N,N-di(bromomethyl) cyclohexane-3,6-dialdehyde-1,2,4,5-tetracarboxylic diimide, N,N-di (chloromethyl)cyclohexane-3,6-dialdehyde-1,2,4,5-tetracarboxylic diimide, N,N-di(iodomethyl)cyclohexane-3,6-dialdehyde-1,2,4,5-tetracarboxylic diimide, N,N-di (hydroxymethyl)cyclohexane-3,6-dialdehyde-1,2,4,5-tetracarboxylic diimide, N,N-di(thiolmethyl) cyclohexane- 3,6-dialdehyde-1,2,4,5-tetracarboxylic diimide, N,N-di(cyanomethyl)cyclohexane-3,6-dialdehyde-1,2,4,5-tetracarboxylic diimide, N,N-di(sulfonic acid methyl)cyclohexane-3,6-dialdehyde-1,2,4,5-tetracarboxylic diimide, N,N-di(carboxylic acid methyl) cyclohexane-3,6-dialdehyde-1,2,4,5-tetracarboxylic diimide, N,N-diphenylcyclohexane-3,6-dinitro-1,2,4,5-tetracarboxylic diimide, N,N-diphenylcyclohexane hexacarboxylic acid-3,6-dichloride-1,2,4,5-tetracarboxylic diimide, N,N-bis(p-hydroxylphenyl)cyclohexane-3,6-dinitro-1,2,4,5-tetracarboxylic diimide, N,N-bis(p-thiolphenyl)cyclohexane-3,6-dinitro-1,2,4,5-tetracarboxylic diimide, N,N-bis(p-bromophenyl)cyclohexane-3,6-dinitro-1,2,4,5-tetracarboxylic diimide, N,N-bis(p-iodophenyl)cyclohexane-3,6-dinitro-1,2,4,5-tetracarboxylic diimide, N,N-bis(p-chlorophenyl) cyclohexane-3,6-dinitro-1,2,4,5-tetracarboxylic diimide, N,N-bis (p-aldehydephenyl)cyclohexane-3,6-dinitro-1,2,4,5-tetracarboxylic diimide, N,N-bis(p-cyanophenyl)cyclohexane-3,6-dinitro-1,2,4,5-tetracarboxylic diimide, N,N-bis(p-carboxylic acid ester phenyl) cyclohexane-3,6-dinitro-1,2,4,5-tetracarboxylic diimide, N,N-bis (p-carboxylic acid phenyl)cyclohexane-3,6-dinitro-1,2,4,5-tetracarboxylic diimide, N,N-dibenzylcyclohexane-3,6-dinitro-1,2,4,5-tetracarboxylic diimide, N,N-bis(p-sulfonic acid phenyl)cyclohexane-3,6-dinitro-1,2,4,5-tetracarboxylic diimide, N,N-di(bromomethyl)cyclohexane-3,6-dinitro-1,2,4,5-tetracarboxylic diimide, N,N-di(chloromethyl)cyclohexane-3,6-dinitro-1,2,4,5-tetracarboxylic diimide, N,N-di(iodomethyl)cyclohexane-3,6-dinitro-1,2,4,5-tetracarboxylic diimide, N,N-di(hydroxymethyl)cyclohexane-3,6-dinitro-1,2,4,5-tetracarboxylic diimide, N,N-di (thiolmethyl)cyclohexane-3,6-dinitro-1,2,4,5-tetracarboxylic diimide, N,N-di(cyanomethyl)cyclohexane-3,6-dinitro-1,2,4,5-tetracarboxylic diimide, N,N-di(sulfonic acid methyl)cyclohexane-3,6-dinitro-1,2,4,5-tetracarboxylic diimide, N,N-di(carboxylic acid methyl)cyclohexane-3,6-dinitro-1,2,4,5-tetracarboxylic diimide, N,N-di(carboxylic acid ester methyl)cyclohexane-3,6-dinitro-1,2,4,5-tetracarboxylic diimide, N,N-di(carboxylic acid ester methyl)cyclohexane-3,6-dinitro-1,2,4,5-tetracarboxylic diimide, and N,N-diphenylcyclohexane hexacarboxylic-3,6-dichloride-1,2,4,5-imide.

12. A cyclohexane-1,2,4,5-diimide derivative selected from the group consisting of N,N-diphenylcyclohexane-3,6-diozonide-1,2,4,5-tetracarboxylic diimide, N,N-diphenylcyclohexane-3,6-dialdehyde-1,2,4,5-tetracarboxylic diimide, N,N-diphenylcyclohexanehexacarboxylic-1,2,4,5-diimide, N,N'-bis(p-sulfonic acid phenyl)cyclohexanehexacarboxylic-1,2,4,5-diimide, N,N'-bisbenzylcyclohexanecarboxylic-1,2,4,5-diimide, and N,N'-diphenylcyclohexanehexacarboxylic-3,6-diacid chloride-1,2,4,5-diimide.

* * * * *